United States Patent
Vinod Muthachikavil et al.

(10) Patent No.: US 12,203,599 B2
(45) Date of Patent: Jan. 21, 2025

(54) METHOD AND SYSTEM FOR IDENTIFICATION OF MATERIALS FOR HYDROGEN STORAGE

(71) Applicant: Tata Consultancy Services Limited, Mumbai (IN)

(72) Inventors: Aswin Vinod Muthachikavil, Pune (IN); Venkata Sudheendra Buddhiraju, Pune (IN); Venkataramana Runkana, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 957 days.

(21) Appl. No.: 17/194,032

(22) Filed: Mar. 5, 2021

(65) Prior Publication Data
US 2021/0293381 A1 Sep. 23, 2021

(30) Foreign Application Priority Data
Mar. 5, 2020 (IN) .............................. 202021009559

(51) Int. Cl.
*F17C 11/00* (2006.01)
*C01B 3/06* (2006.01)
(Continued)

(52) U.S. Cl.
CPC ............ *F17C 11/005* (2013.01); *C01B 3/065* (2013.01); *G06N 20/00* (2019.01); *G16C 20/30* (2019.02); *F17C 2221/012* (2013.01)

(58) Field of Classification Search
CPC .. F17C 11/005; F17C 2221/012; G16C 20/30; G16C 60/00; G16C 20/70;
(Continued)

(56) References Cited

U.S. PATENT DOCUMENTS 6,916,563 B2 * 7/2005 Yamamoto .......... H01M 8/0662
429/408
7,736,814 B2 * 6/2010 Igarashi ............ H01M 8/04225
429/429
(Continued)

OTHER PUBLICATIONS

Vajeeston, Ponniah et al., "Predicting New Materials for Hydrogen Storage Application", Journal—Material, 2009, MDPI, https//www.mdpi.com/1996-1944/2/4/2296.
(Continued)

*Primary Examiner* — Shogo Sasaki
(74) *Attorney, Agent, or Firm* — FINNEGAN, HENDERSON, FARABOW, GARRETT & DUNNER LLP

(57) ABSTRACT

Hydrogen being a clean, highly abundant and renewable fuel, is a promising alternative for conventional energy sources. Mostly, this hydrogen is stored in the form of hydrides. The existing methods for identification of material for hydrogen storage as expensive and time consuming. A method and system of identification of materials for hydrogen storage has been provided. The method provides a machine learning technique to predict the hydrogen storage capacity of materials, using only the compositional information of the compound. A random forest model used in the work was able to predict the gravimetric hydrogen storage capacities of intermetallic compounds. The method and system is also configured to predict the thermodynamic stability of the intermetallic compound.

7 Claims, 6 Drawing Sheets

(51) Int. Cl.
*G06N 20/00* (2019.01)
*G16C 20/30* (2019.01)

(58) Field of Classification Search
CPC ........ G16C 20/62; G06N 20/00; C01B 3/065; Y02E 60/36; Y02E 60/32
See application file for complete search history.

(56) References Cited

U.S. PATENT DOCUMENTS

| | | | | |
|---|---|---|---|---|
| 7,855,025 | B2* | 12/2010 | Spare | H01M 8/04097 429/446 |
| 7,943,265 | B2* | 5/2011 | Katano | H01M 8/04231 429/429 |
| 7,998,628 | B2* | 8/2011 | Kanno | H01M 8/04082 429/448 |
| 8,057,948 | B2* | 11/2011 | Takaki | H01M 8/04761 429/444 |
| 8,211,581 | B2* | 7/2012 | Katano | H01M 8/04753 429/444 |
| 8,323,841 | B2* | 12/2012 | Baaser | H01M 8/04328 702/147 |
| 8,703,349 | B2* | 4/2014 | Kanno | H01M 8/0662 429/444 |
| 8,920,984 | B2* | 12/2014 | Janarthanam | H01M 8/04156 429/408 |
| 10,211,471 | B2* | 2/2019 | Shim | H01M 8/04201 |
| 10,236,526 | B2* | 3/2019 | Gilliam | C25B 1/04 |
| 10,443,954 | B1* | 10/2019 | Zidan | F28D 20/003 |
| 11,035,791 | B2* | 6/2021 | Tong | G01N 21/552 |
| 11,060,805 | B2* | 7/2021 | Semenic | H01L 23/3733 |
| 2006/0110640 | A1* | 5/2006 | Yoshida | H01M 8/2457 429/444 |
| 2006/0130651 | A1* | 6/2006 | Bizjak | C01B 3/384 95/96 |
| 2007/0243437 | A1* | 10/2007 | Katano | H01M 8/04097 429/479 |
| 2011/0091352 | A1 | 4/2011 | Fang et al. | |
| 2012/0237843 | A1* | 9/2012 | Paganelli | C25B 15/02 429/444 |
| 2013/0137007 | A1* | 5/2013 | Lee | H01M 8/04447 429/444 |

OTHER PUBLICATIONS

Rahnama, Alireza et al., "Machine learning based prediction of metal hydrides for hydrogen storage, part I: Prediction of hydrogen weight percent", International Journal of Hydrogen Energy, 2019, vol. 44, Issue 14, pp. 7337-7344, Science Direct, https://www.sciencedirect.com/science/article/abs/pii/S0360319919304458.

Hattrick-Simpers, Jason R. et al., "A Simple Constrained Machine Learning Model for Predicting Materials for High Pressure Hydrogen Compression", Molecular Systems Design & Engineering, Apr. 2018, Pubs, https://pubs.rsc.org/en/content/articlelanding/2018/me/c8me00005k#!divAbstract.

* cited by examiner

METHOD AND SYSTEM FOR IDENTIFICATION OF MATERIALS FOR HYDROGEN STORAGE

PRIORITY CLAIM

This U.S. patent application claims priority under 35 U.S.C. § 119 to: India Application No. 202021009559, filed on Mar. 5, 2020. The entire contents of the aforementioned application are incorporated herein by reference.

TECHNICAL FIELD

The embodiments herein generally relate to the field of hydrogen storage. More particularly, but not specifically, the present disclosure provides a method and system for identification of materials for hydrogen storage.

BACKGROUND

Hydrogen being a clean, highly abundant and renewable fuel, is a promising alternative for conventional energy sources like fossil fuel and natural gases. There has been much deliberation on the use of hydrogen instead of fossil fuels leading to the creation of a 'Hydrogen economy'. An important aspect of the hydrogen economy is the storage of hydrogen. Metal hydrides are one of the most important modes of hydrogen storage along with other methods like compression and liquefaction. Hydrogen forms metal hydrides with some metals and alloys leading to solid-state storage under moderate temperature and pressure. Metal hydrides are hence considered to be a volume efficient and safe hydrogen storage method for applications in vehicles. Current researchers are aiming at developing new materials with higher capacities to store hydrogen at moderate temperatures and pressures.

Intermetallic compounds for hydrogen storage are often prepared by combining (one or more) elements forming a stable hydride (part A) with (one or more) elements forming a nonstable hydride (part B). Some of these alloys readily form stable hydrides as well as release hydrogen at moderate temperatures and pressures becoming attractive candidates for storing hydrogen. Development of a model to predict the hydrogen storage capacities can provide a new means of screening materials with good performance before investing time and money into experimental investigations. The typical time frame reported for discovering a material to its deployment is 10-20 years.

In the field of materials science, the two major areas in which machine learning finds application are: (a) prediction of material properties and (b) discovery of new materials for specific applications. The field of materials discovery has also been impacted widely by machine learning. Some noteworthy works include design of new guanidinium ionic liquids, finding nature's missing ternary oxides, discovery of new compounds with ionic substitutions, and using failed experiments in the discovery of materials.

An important drawback of using machine learning in the arena of materials discovery, is that the models sometimes predict hypothetical compounds that might be unstable in nature. In this regard, there haves been few studies that look for compounds keeping in mind their thermodynamic stability.

The existing prior art lacks in its ability to make best use of the knowledge of existing materials in simplifying the process of identification of new hydrogen storage materials. The existing methods used for the identification of materials consume a lot of time and resources. These methods involve trial and error combination of different metals. This can lead to a large number of potential candidates based on the possible combination of different metals. Conducting experiments on each of these candidates requires high investments in terms of time and resources. In addition to that the existing prior art involves the use of molecular simulations for property estimation. This requires information on the structure of molecule, which is generally not available for a new compound a priory.

SUMMARY

Embodiments of the present disclosure present technological improvements as solutions to one or more of the above-mentioned technical problems recognized by the inventors in conventional systems.

In view of the foregoing, an embodiment herein provides a system for identification of compounds for hydrogen storage. The system comprises an input module, one or more hardware processors and a memory in communication with the one or more hardware processors. The input module provides a first set of one or more elements and a second set of one or more elements. The memory further comprises a compound generation unit, a hydrogen storage capacity prediction unit and a stability analysis unit. The compound generation unit generates a plurality of compounds using the first set of one or more elements and a second set of one or more elements based on predefined input conditions, wherein the plurality of compounds are expected to have high hydrogen storage capabilities. The hydrogen storage capacity prediction unit generates molecular descriptors for the plurality of compounds by extracting compositional information of each of the plurality of compounds, generates a machine learning model using the molecular descriptors, predict gravimetric hydrogen storage capacity of the generated plurality of compounds using the machine learning model, and selects a set of compounds out of the plurality of compounds based on a predefined criteria of gravimetric hydrogen storage capacity. The stability analysis unit predicts formation energy of each of the set of compounds using a computational database of formation energies, calculates minimum formation energy of all possible decomposition mixtures of each of the set of compounds, and identifies the compound as stable if the formation energy of the compound is less than the minimum of the formation energies of each possible decomposition mixture of the respective compound, after which each of the compounds marked as stable are identified as compounds suitable for hydrogen storage.

In another aspect, the embodiment here provides a method for identification of compounds for hydrogen storage. Initially, a first set of one or more elements are provided via an input module. Similarly, a second set of one or more elements are also provided via the input module. Further, a plurality of compounds is generated using the first set of one or more elements and the second set of one or more elements based on predefined input conditions, wherein the plurality of compounds are expected to have hydrogen storage capabilities. In the next step, molecular descriptors are generated for the plurality of compounds using compositional information of each of the plurality of compounds. Further, a machine learning model is generated using the molecular descriptors. In the next step, gravimetric hydrogen storage capacity of the generated plurality of compounds is predicted using the machine learning model. In the next step, a set of compounds is selected out of the plurality of compounds based on a predefined criteria of gravimetric hydrogen storage capacity. In the next step formation energy of each of the set of compounds is predicted using a computational database of formation energies. Further, minimum formation energy of all possible decomposition mixtures of each compound is also calculated. And finally, the compound is identified as stable if the formation energy of the compound is less than the minimum of the formation energies of the possible decomposition mixtures of the respective compound, wherein each of the stable compounds is identified as the compound for hydrogen storage.

In another aspect the embodiment here provides one or more non-transitory machine readable information storage mediums comprising one or more instructions which when executed by one or more hardware processors cause identification of compounds for hydrogen storage. Initially, a first set of one or more elements are provided via an input module. Similarly, a second set of one or more elements are also provided via the input module. Further, a plurality of compounds is generated using the first set of one or more elements and the second set of one or more elements based on predefined input conditions, wherein the plurality of compounds are expected to have hydrogen storage capabilities. In the next step, molecular descriptors are generated for the plurality of compounds using compositional information of each of the plurality of compounds. Further, a machine learning model is generated using the molecular descriptors. In the next step, gravimetric hydrogen storage capacity of the generated plurality of compounds is predicted using the machine learning model. In the next step, a set of compounds is selected out of the plurality of compounds based on a predefined criteria of gravimetric hydrogen storage capacity. In the next step formation energy of each of the set of compounds is predicted using a computational database of formation energies. Further, minimum formation energy of all possible decomposition mixtures of each compound is also calculated. And finally, the compound is identified as stable if the formation energy of the compound is less than the minimum of the formation energies of the possible decomposition mixtures of the respective compound, wherein each of the stable compounds is identified as the compound for hydrogen storage. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

The accompanying drawings, which are incorporated in and constitute a part of this disclosure, illustrate exemplary embodiments and, together with the description, serve to explain the disclosed principles.

DETAILED DESCRIPTION

Figure 1:
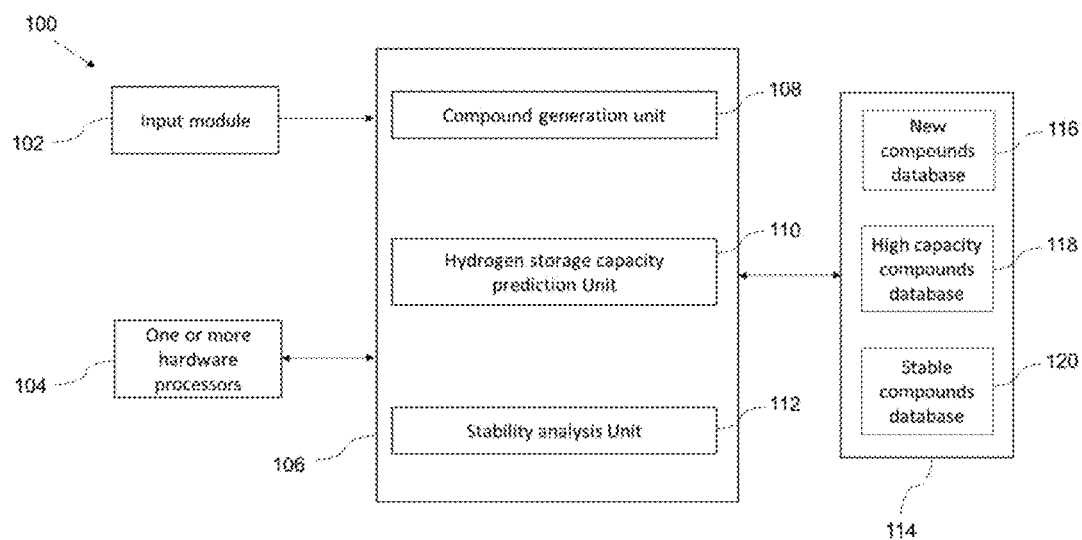
FIG. 1 shows a block diagram of a system for identification of compounds for hydrogen storage according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Referring now to the drawings, and more particularly to FIG. 1 through FIG. 5, where similar reference characters denote corresponding features consistently throughout the figures, there are shown preferred embodiments and these embodiments are described in the context of the following exemplary system and/or method.

According to an embodiment of the disclosure, a system 100 for identification of materials for hydrogen storage is shown in the block diagram of FIG. 1. Normally the materials include various compounds. Though in most of the cases these compounds are referred to as intermetallic compounds, these compounds may also be prepared using few non-metals such as Silicon etc. For the sake of description in this disclosure, all the materials are referred to as intermetallic compounds. Intermetallic compounds for hydrogen storage have two parts in them, part A and part B. Part A predominantly contains element(s) which form stable hydrides. Part B contains element(s) which form unstable hydrides. Some of these alloys readily form stable hydrides as well as release hydrogen at moderate temperatures and pressures, becoming attractive candidates for storing hydrogen. The system 100 is configured to identify the intermetallic compounds with high hydrogen storage capacities. The system 100 is also configured to predict the thermodynamic stability of the intermetallic compound.

According to an embodiment of the disclosure, the system 100 comprises an input module 102, one or more hardware processors 104 and a memory 106 in communication with the one or more hardware processors 104 as shown in the block diagram of FIG. 1. The one or more hardware processors 104 work in communication with the memory 106. The one or more hardware processors 104 are configured to execute a plurality of algorithms stored in the memory 106. The memory 106 further includes a plurality of modules for performing various functions. The memory 106 comprises a compound generation unit 108, a hydrogen storage capacity prediction unit 110 and a stability analysis unit 112. The memory 106 may further comprise other modules for performing certain functions. The system 100 also comprises a database 114 for storing various compounds. The database 114 further comprises a new compound database 116, a high capacity compounds database 118, and a stable compounds database 120.

According to an embodiment of the disclosure, the input module 102 (Input/Output interface) is configured to provide a first set of one or more elements and a second set of one or more elements to the system 100. The input module 102 is accessible to the user via smartphones, laptop or desktop configuration thus giving the user the freedom to interact with the system 100 from anywhere anytime. The I/O interface 102 may include a variety of software and hardware interfaces, for example, interfaces for peripheral device (s), such as a keyboard, a mouse, an external memory, a camera device, and a printer. The I/O interface 102 can facilitate multiple communications within a wide variety of networks and protocol types, including wired networks, for example, local area network (LAN), cable, etc., and wireless networks, such as Wireless LAN (WLAN), cellular, or satellite.

According to an embodiment of the disclosure, the memory 106 comprises the compound generation unit 108. The compound generation unit 108 is configured to generate a plurality of compounds using the first set of one or more elements and a second set of one or more elements based on a set of predefined input conditions. Each of the plurality of compounds are probable to have hydrogen storage capabilities. The plurality of compounds generated using the compound generation unit 108 is stored in the new compounds database 116. The compound generation unit 108 develops a library of probable compositions using combinatorial (and/or probabilistic) methods. The compound generation unit 108 uses the knowledge of existing composition of hydrogen storage materials with high storage capacities, to generate compositions for probable intermetallic compounds.

Figure 2:
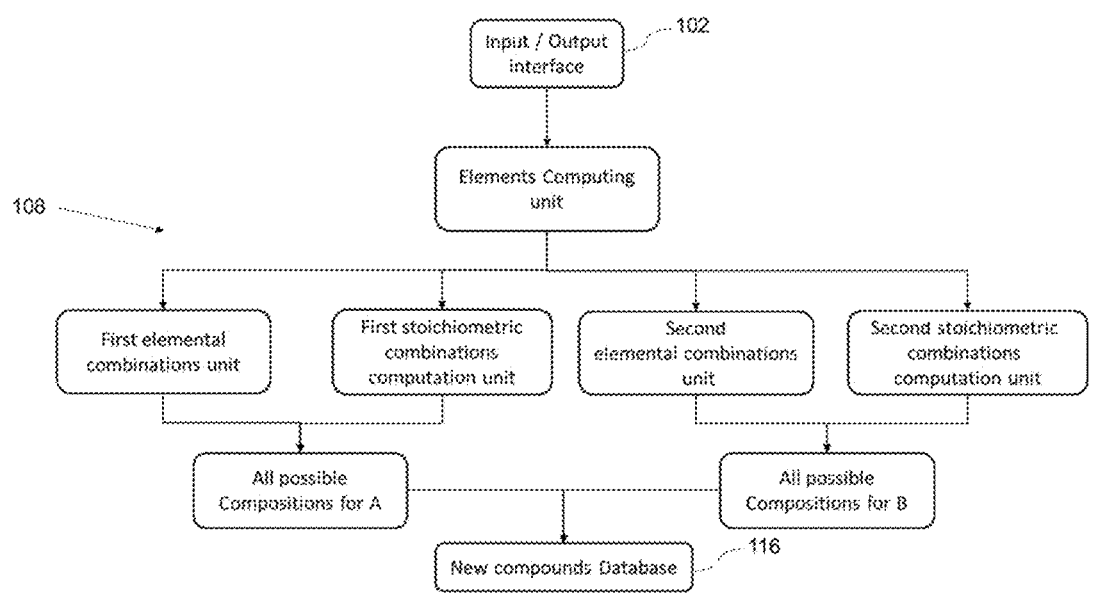
FIG. 2 shows a schematic block diagram of a compound generation unit of the system of FIG. 1 according to an embodiment of the present disclosure.

A schematic block diagram for the compound generation unit 108 is shown in FIG. 2. The compound generation unit 108 receives the first set of elements, the second set of elements, total number of elements in the compound, type of compound and incremental steps in stoichiometric coefficient as input from the input/output interface 102. An elements computing unit computes the number of elements in the first set and the second set of elements. The first set of elements and the second set of elements are provided as input to the four different units, i.e., a first elemental combinations unit, a first stoichiometric combinations computation unit, a second elemental combinations unit and a second stoichiometric combinations computation unit. Based on the predefined input conditions, all possible intermetallic compounds are generated, i.e., all possible combinations for part A is generated using the first elemental combinations unit the first stoichiometric combinations computation unit. And the possible combinations for part B is generated using the second elemental combinations unit and the second stoichiometric combinations computation unit. Where part A has one or more of the first set of elements and part B has one or more of the second set of elements, other than those that comprise part A. A new set of compounds is generated based on the possible elemental combinations and stoichiometric numbers and are stored in the new compounds database 116.

According to an embodiment of the disclosure, the memory 106 comprises the hydrogen storage capacity prediction 110. The hydrogen storage capacity prediction 110 is configured to generate molecular descriptors for the plurality of compounds by extracting information of a composition of each the plurality of compounds, generate a machine learning model using the molecular descriptors, predict gravimetric hydrogen storage capacity of the generated plurality of compounds using the machine learning model, and select a set of compounds out of the plurality of compounds based on a predefined criteria of gravimetric hydrogen storage capacity. The set of compounds is stored in the high capacity compounds database 118.

The hydrogen storage capacity prediction 110 is a data-based module and makes use of machine learning algorithms like support vector machines, random forests and/or other such models. Molecular descriptors that can represent each molecule uniquely are generated from a set of elemental descriptors. The set of elemental descriptors is listed in Table 1, but not limited to it. Corresponding to each elemental descriptor, the average, maximum, minimum and the range of the value was computed over the whole compound, part A of the compound and part B of the compound separately. However the molecular descriptors calculation need not be limited to the above mentioned quantities. These set of descriptors can effectively describe molecules for the purpose of predicting the hydrogen storage capacities of materials. Out of the generated set of descriptors, those that can best predict the property of interest are selected. The model is trained based on the set of descriptors chosen to predict the hydrogen storage capacities of intermetallic compounds of the type AB, $AB_2$, $A_2B$ and $AB_5$.

TABLE 1

Descriptors of constituent elements

| S. No | Descriptor of constituent element |
|---|---|
| 1 | Atomic number |
| 2 | Atomic weight |
| 3 | Group number |
| 4 | Period number |
| 5 | Empirical atomic radius (pm) |
| 6 | Calculated atomic radius (pm) |
| 7 | Covalent radius |
| 8 | Pauling electronegativity |
| 9 | Valence |
| 10 | Outer shell s electron |
| 11 | Outer shell p electron |
| 12 | Outer shell d electron |
| 13 | Outer shell electron |
| 14 | First ionization energy (KJ/mol) |
| 15 | Second ionization energy (KJ/mol) |
| 16 | Third ionization energy (KJ/mol) |
| 17 | Melting point (K) |
| 18 | Boiling point (K) |
| 19 | Density (g/cc) |

The empirical relation between the heats of formation of metal hydrides and the electronic band structure is well known in literature.

Figure 5:
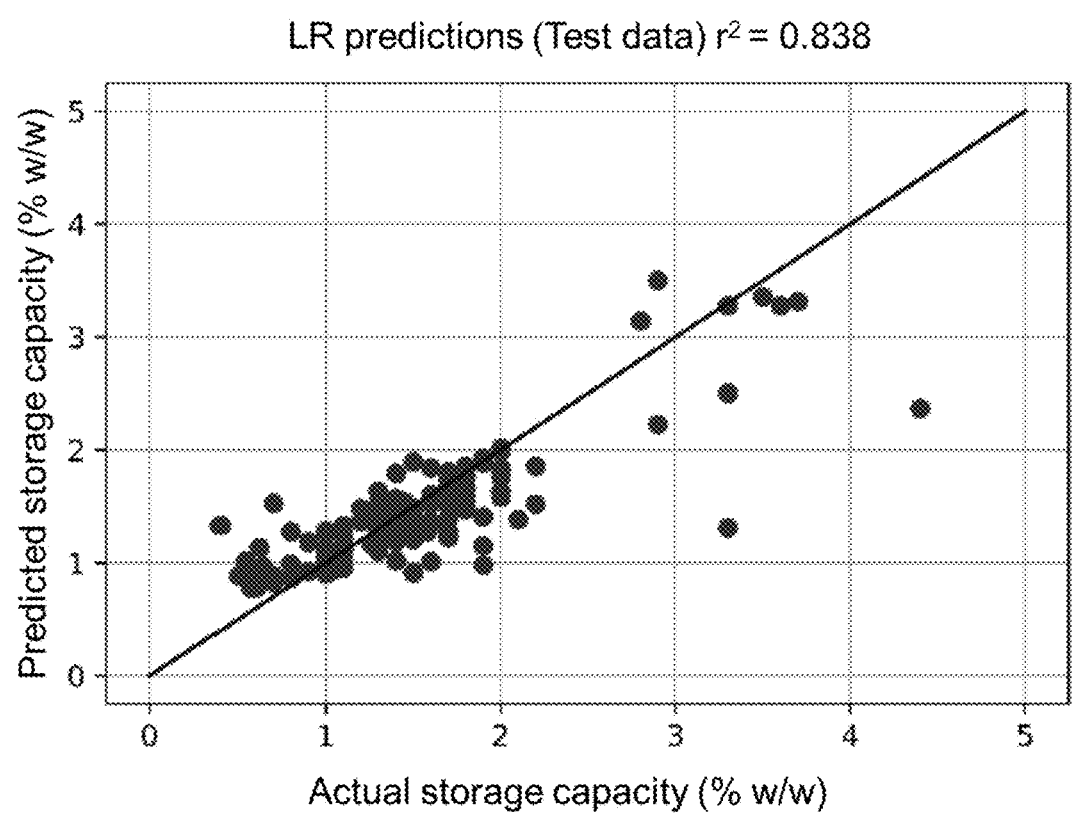
FIG. 5 shows final fit of the random forest model predictions according to an embodiment of the present disclosure.

Using this correlation, the elemental descriptors that are important for calculating the bandgap of materials can also be utilized in calculating the hydrogen storage capacities of inorganic compounds. Hence, a subset of elemental descriptors used to predict the bandgap of inorganic solids was used to calculate the molecular descriptors in the present disclosure. The 19 elemental descriptors chosen for the hydrogen storage capacity prediction unit 110 is listed in TABLE 1. Corresponding to each elemental descriptor, the average, maximum, minimum and the range of the value was computed over the whole compound, part A of the compound and part B of the compound separately. Another molecular descriptor that was considered was the presence of multiple plateaus in the hydrogen storage characteristic curve of the compound (descriptor value set to 1 when multiple plateaus were observed, and 0 otherwise). The results as shown in FIG. 5 show that the random forest model is able to predict the hydrogen storage capacities of materials (which it has not seen before) fairly well, with an $r^2$ value of about 0.838 and an absolute error of 0.24+/−0.08 (percentage storage capacity, weight/weight).

The hyper parameters of the hydrogen storage capacity prediction 110 were tuned by performing a 2-stage optimization procedure. The first step was the random search step using 3-fold cross validation (on the training data) to estimate the best combination of parameters. The model was further optimized by doing a grid search around the best combination of the parameters suggested by the random search.

According to an embodiment of the disclosure, the memory 106 comprises the stability analysis unit 112. The stability analysis unit 112 is configured to further screen the probable materials that are predicted to have high hydrogen storage capacities. All the high capacity compounds may or may not be thermodynamically stable, and hence screening out the unstable ones is essential to narrow down the probable list, saving resources and effort. The compositional information of the high capacity materials is sent to the stability analysis unit. The thermodynamically stable compounds are then stored in the stable compounds database 120. This module makes use of machine learning based techniques to check the compound as thermodynamically stable or not.

Figure 3:
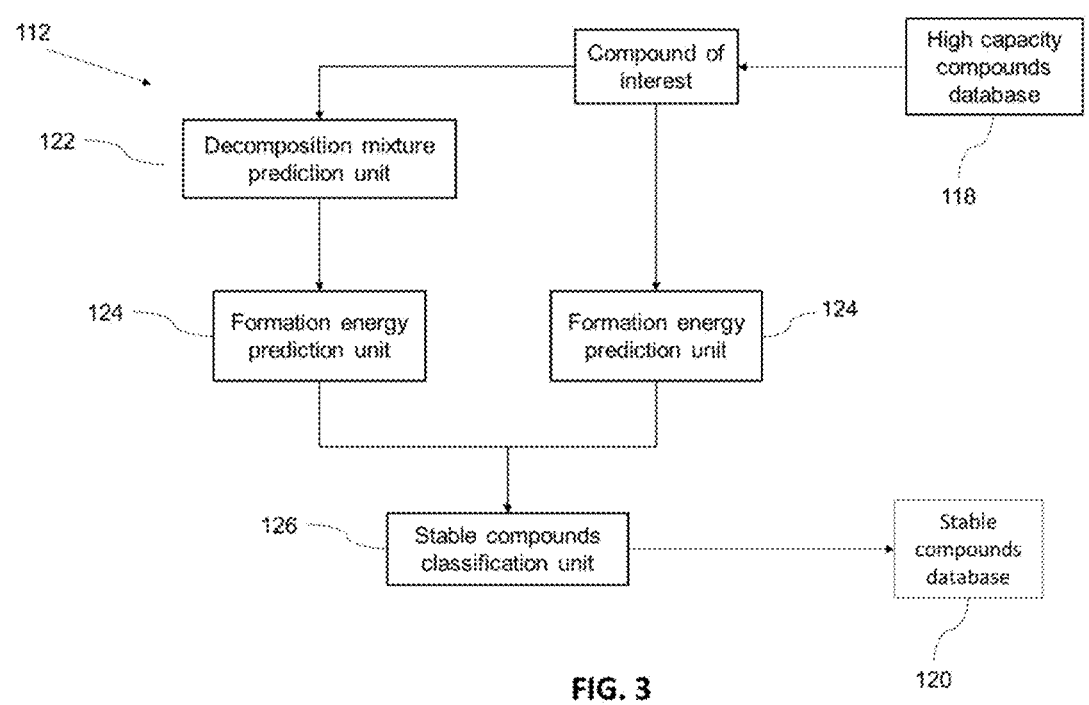
FIG. 3 shows a schematic block diagram of a stability analysis unit of the system of FIG. 1 according to an embodiment of the present disclosure.

A schematic block diagram of the stability analysis unit 112 is shown in FIG. 3. A compound of interest is taken as input from the high capacity compounds database 118. A formation energy prediction unit 124 predicts the formation energy of each of the set of compounds using a computational database of formation energy. Further a minimum of the formation energies of all possible decomposition mixtures of each compound is calculated using the decomposition mixture prediction unit 122 and the formation energy prediction unit 124. Further, the stable compounds classification unit 126 is configured to identify the compound as stable if the formation energy of the compound is less than the minimum computed as described above. Each of the compounds labelled herein as stable is identified as a compound suitable for hydrogen storage. The stable compounds are then stored in the stable compounds database 120.

Figure 4A:
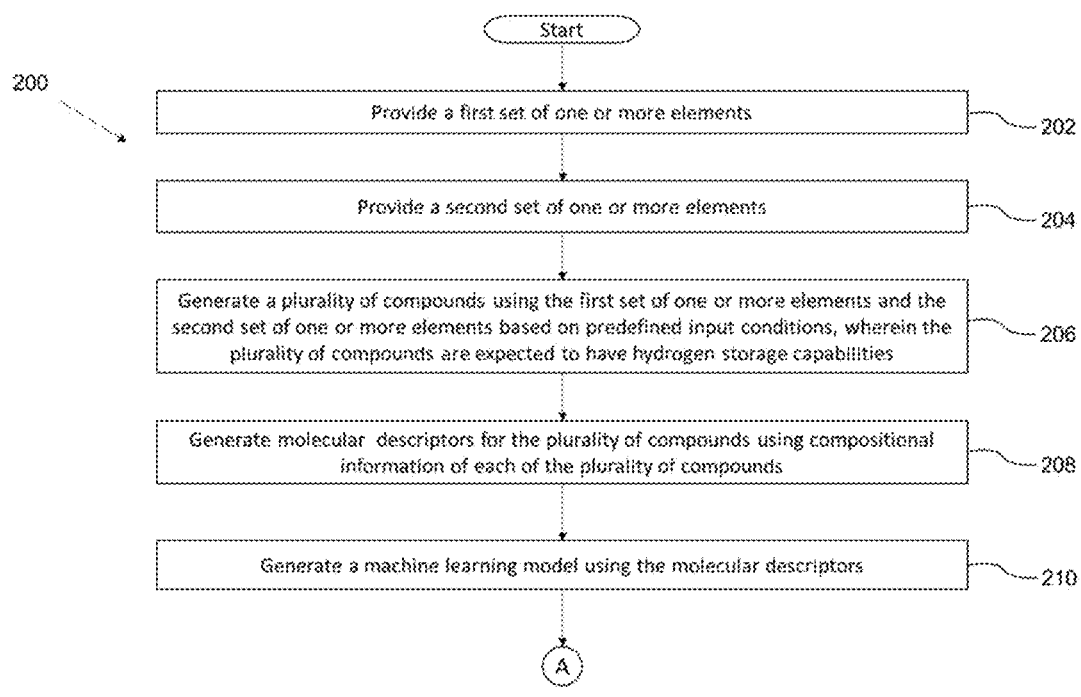
FIGS. 4A-4B show a flowchart illustrating the steps involved in identification of compounds for hydrogen storage according to an embodiment of the present disclosure.
Figure 4B:
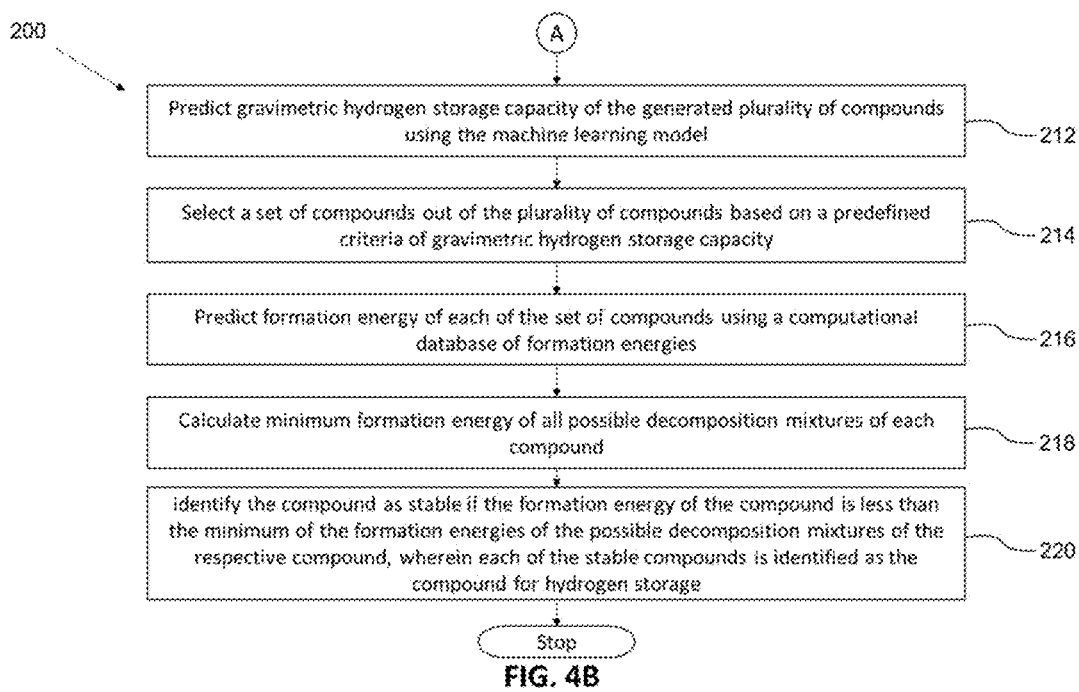

In operation, a flowchart 200 illustrating a method for identification of compounds for hydrogen storage is shown in FIG. 4A-4B. Initially at step 202, the first set of one or more elements is provided by the input module 102. Similarly, at step 204, the second set of one or more elements is also provided. At step 206, the plurality of compounds are generated using the first set of one or more elements and the second set of one or more elements based on predefined input conditions. The plurality of compounds are expected to have high hydrogen storage capabilities. The predefined input conditions comprise type of compound, first and second set of one or more elements, total number of elements in the compound and incremental steps in stoichiometric coefficient.

At step 208, molecular descriptors are generated for the plurality of compounds by extracting information of a composition of each the plurality of compounds. The molecular descriptors can be generated using the set of elemental descriptors as shown in TABLE 1. At step 210, a machine learning model is generated using the molecular descriptors. Further at step 212, gravimetric hydrogen storage capacity of the generated plurality of compounds is predicted using the machine learning model. At step 214, a set of compounds is selected out of the plurality of compounds based on a predefined criteria of gravimetric hydrogen storage capacity. Thus this step further reduces the total number of probable compounds that can be passed onto the stability analysis unit 112.

In the next step 216, the formation energy of each of the selected set of compounds is predicted using a machine learning model trained on computational database of formation energies. At step 218, a minimum of the formation energies of all possible decomposition mixtures of a given compound is calculated. And finally, at step 220, the compound is identified as stable if the formation energy of the compound is less than the minimum calculated as described above. Each of the stable compounds determined as such is identified as a suitable compound for hydrogen storage.

According to an embodiment of the disclosure, the system 100 can also be explained with the help of following example. The metal hydride database published by U.S. Department of Energy (U.S. DOE) and Sandia National Laboratories (presented to the International Energy Agency Hydrogen Implementing Agreement (IEA-HIA) [17]) has over 2000 entries and was used for the example provided in present disclosure. For any given compound, the value of hydrogen storage capacity recorded in the database corresponds to the one measured at the highest pressure and lowest temperature. The entries of type $AB_5$, $AB_2$, $AB$, $A_2B$ (excluding complex hydrides) along with their reported hydrogen storage capacities and the ambient pressure and temperatures, were filtered out to obtain 700 compounds that were used for the study. The data has been filtered such that the compounds with gravimetric hydrogen storage capacities from 0.3 to 5.5 weight percentage have been selected.

The empirical relation between the heats of formation of metal hydrides and the electronic band structure is given in the equation no. (1):

$$\Delta H = \frac{n_s}{2}[\alpha(E_F - E_S) - \beta] \quad (1)$$

Where,
$n_s$=2 for alkali metals, 1 for other metals
$E_s$=Energy of the lowest conduction band of host metal
$E_F$=Fermi level of the host metal
$\propto$, $\beta$=Constants determined by fitting experimental values
From the above empirical relation, it can be inferred that the descriptors which have an effect on the bandgap may also be relevant for predicting the hydrogen storage capacity of materials. 34 elemental descriptors are useful in predicting the band gap of materials. Hence, a subset of the 34 elemental descriptors is chosen for the example of present disclosure, as listed in TABLE 1. The values of each descriptor were extracted from databases and open sources.

Corresponding to each elemental descriptor, the average, maximum, minimum and range were computed for the whole compound. These values were also computed for part A of the compound and part B of the compound separately. Another descriptor that was considered was the presence of multiple plateaus in the hydrogen storage characteristic curve of the compound (descriptor value set to 1 when multiple plateaus were observed, and 0 otherwise). In all, 229 molecular descriptors were computed as mentioned above. Along with temperature (non-molecular feature), a total of 230 features for the 700 compounds were computed. Deleting the ones with zero entries brings down this number to a total of 224 features that could then be used to sufficiently describe each entry in the database.

Furthermore, the values of all the features were adjusted such that the maximum value is scaled up to 1 and the minimum value is scaled down to 0. This ensures that the machine learning algorithms do not give undue importance to features with higher magnitudes. However, the target variable (Hydrogen storage capacity) was not scaled.

Calculation of feature importance: 3600 different random forest models were fit to the data, and the feature importance computed for the best fitting 20 models was averaged to compute the importance of each feature. The optimal number of features is determined by iterating the number of features in the descending order of their importance and computing the $r^2$ value of the fit. The optimal number of features for building the model is determined by the maximum value of the $r^2$ value obtained. However, the models built with optimized number of principal components were observed to be lesser efficient to predict the hydrogen storage capacity, when compared to the ones built with optimal number of pure features.

Further, the hyper parameters were tuned for machine learning models performing a 2 stage optimization procedure. The first step was a random search of different combinations of those parameters that were to be optimized. The ranges of these parameters are described in TABLE 2. With random different combination of parameters, three fold cross validation was used (on the training data) to build model, and the ability of the model to predict the hydrogen storage capacity was estimated. The combination of parameters giving the best model is further optimized by doing a grid search around the parameters suggested by the random search. Though it should be appreciated that the use of any other machine learning method is well within the scope of this disclosure.

TABLE 2

Parameters tuned for model optimization

| Model | Parameters | Parameter value |
|---|---|---|
| Random Forest | Number of trees in the forest | 50-2000 |
| | Maximum number of features considered for splitting a node | Auto/Square root |
| | Maximum number of levels in each decision tree | 10-110 |
| | Minimum number of data points placed in a node before the node is split | 2, 5, 10 |
| | Bootstrap method | True, False |
| Support vector Regressor | Kernel | Linear, poly, rbf |
| | Gamma | 10-4, 10-3, 0.01, 0.1 0,2, 0.5, 0.6, 0.9 |
| | C | 1, 10, 100, 1000 10000 |

Results

To check the performance of the model in predicting the hydrogen storage capacities of material unseen by the model, the hydrogen storage capacities of the compounds that were not seen by the model before were predicted. As shown in FIG. 5, the results show that the random forest model is able to predict fairly well with an $r^2$ value of about 0.838 and an absolute error of 0.24±0.08 (percentage storage capacity, weight/weight). The other models (SVR and linear regressor) are less accurate in comparison to the random forest model. It should however be noted that the accuracy of the model is higher for materials with hydrogen storage capacities lesser than 2.5 wt. %. The model tends to underpredict the hydrogen storage capacities of materials with capacities more than 2.5 wt. %. This could be attributed to the lesser availability of data in this range.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of the present disclosure herein solve the problems of intensive and time taking research required for identification of new hydrogen storage material. The disclosure provides a method and system for identification of materials for hydrogen storage.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for identification of compounds for hydrogen storage, the processor implemented method comprising:
providing, via an input module, a first set of one or more elements;
providing, via the input module, a second set of one or more elements;
generating, via one or more hardware processors, a plurality of compounds using the first set of one or more elements and the second set of one or more elements based on predefined input conditions, wherein the predefined input conditions comprises: type of compounds, a list of elements in the first set of one or more elements, a list of elements in the second set of one or more elements, and a total number of elements desired in the compound, the type of compounds comprising one of AB, $AB_2$, $A_2B$, and $AB_5$, part A being selected from the first set of one or more elements provided and part B being selected from the second set of one or more elements provided that do not constitute A, wherein the plurality of compounds have hydrogen storage capabilities, and wherein generation of the plurality of compounds develops a library of probable compositions using knowledge of existing composition of hydrogen storage materials with high storage capacities;

generating, via the one or more hardware processors, molecular descriptors for the plurality of compounds by extracting compositional information of each of the plurality of compounds, wherein the molecular descriptors effectively describe molecules for the purpose of predicting hydrogen storage capacities of materials, wherein generating the molecular descriptors comprises:

selecting a subset of elemental descriptors of the molecular descriptors which have an effect on bandgap of materials; and generating the molecular descriptors using the subset of elemental descriptors, the molecular descriptors represent each molecule uniquely from the set of elemental descriptors;

generating, via the one or more hardware processors, a machine learning model using the molecular descriptors;

predicting, via the one or more hardware processors, gravimetric hydrogen storage capacity of the generated plurality of compounds using the machine learning model, wherein the machine learning model, is trained via the one or more hardware processors, based on the molecular descriptors chosen to predict the hydrogen storage capacities of the plurality of compounds, wherein predicting the gravimetric hydrogen storage capacity further comprises providing feedback to improve prediction, and wherein the prediction of the gravimetric hydrogen storage capacity comprises:

training the machine learning model based on the molecular descriptors for predicting the gravimetric hydrogen storage capacity of the generated plurality of compounds, and optimizing the machine learning model by performing a two-stage optimization procedure comprising a three-fold cross validation for estimating a combination of parameters and a grid search on the estimated combination of parameters;

selecting, via the one or more hardware processors, a set of compounds out of the plurality of compounds based on a predefined criteria of gravimetric hydrogen storage capacity, wherein the selecting step reduces total number of probable compounds;

predicting, via the one or more hardware processors, formation energy of each of the set of compounds using a computational database of formation energies;

calculating, via the one or more hardware processors, minimum formation energy of all possible decomposition mixtures of each compound of the set of compounds; and predicting, via the one or more hardware processors, a compound as thermodynamically stable in response to determining that the formation energy of the compound is less than the minimum of the formation energies of the possible decomposition mixtures of the respective compound, wherein each of the thermodynamically stable compounds is identified as the compound suitable for hydrogen storage, and wherein the thermodynamic stability of the compound is analyzed based on a machine learning model built from an available database of compound formation energies using a DFT simulation database.

2. The processor implemented method of claim 1, further comprising selecting a set of relevant features out of the available molecular descriptors, wherein the set of features is configured to predict property of interests.

3. The processor implemented method of claim 1, wherein the molecular descriptors are calculated using one or more of atomic number, an atomic weight, a group number, a period number, an empirical atomic radius, a calculated atomic radius, a covalent radius, Pauling electronegativity, valence, an outer shell s electrons, an outer shell p electrons, an outer shell d electrons, an outer shell electrons, a first ionization energy, a second ionization energy, a third ionization energy, a melting point, a boiling point or density.

4. A system for identification of compounds for hydrogen storage, the system comprises:

an input module for providing a first set of one or more elements and a second set of one or more elements;

one or more hardware processors; and a memory in communication with the one or more hardware processors, the memory further comprises:

a compound generation unit configured to generate a plurality of compounds using the first set of one or more elements and the second set of one or more elements based on predefined input conditions, wherein the predefined input conditions comprises: type of compounds, a list of elements in the first set of one or more elements, a list of elements in the second set of one or more elements, and a total number of elements desired in the compound, the type of compounds comprising one of AB, $AB_2$, $A_2B$, and $AB_5$, part A being selected from the first set of one or more elements provided and part B being selected from the second set of one or more elements provided that do not constitute A, wherein the plurality of compounds have hydrogen storage capabilities, and wherein the compound generation unit develops a library of probable compositions by using knowledge of existing composition of hydrogen storage materials with high storage capacities;

a hydrogen storage capacity prediction unit configured to:

generate molecular descriptors for the plurality of compounds by extracting compositional information of each of the plurality of compounds, wherein the molecular descriptors effectively describe molecules for the purpose of predicting hydrogen storage capacities of materials, wherein to generate the molecular descriptors, the hydrogen storage capacity prediction unit is configured to:

select a subset of elemental descriptors of the molecular descriptors which have an effect on bandgap of materials; and generate the molecular descriptors using the subset of elemental descriptors, the molecular descriptors represent each molecule uniquely from the set of elemental descriptors;

generate a machine learning model using the molecular descriptors, predict gravimetric hydrogen storage capacity of the generated plurality of compounds using the machine learning model, wherein the machine learning model is trained based on the molecular descriptors chosen to predict the hydrogen storage capacities of the plurality of compounds, wherein predicting the gravimetric hydrogen storage capacity further comprises providing feedback to improve prediction, and wherein for the prediction of the gravimetric hydrogen storage capacity, the hydrogen storage capacity prediction unit is configured to:
  train the machine learning model based on the molecular descriptors for predicting the gravimetric hydrogen storage capacity of the generated plurality of compounds, and
  optimize the machine learning model by performing a two-stage optimization procedure comprising a three-fold cross validation for estimating a combination of parameters and a grid search on the estimated combination of parameters;
select a set of compounds out of the plurality of compounds based on a predefined criteria of gravimetric hydrogen storage capacity, wherein selecting step reduces total number of probable compounds; and
a stability analysis unit configured to:
  predict formation energy of each of the set of compounds using a computational database of formation energies,
  calculate minimum formation energy of all possible decomposition mixtures of each of the set of compounds, and
  predict a compound as thermodynamically stable in response to determining that the formation energy of the compound is less than the minimum of the formation energies of each possible decomposition mixture of the respective compound, after which each of the compounds marked as thermodynamically stable are identified as compounds suitable for hydrogen storage, and wherein the thermodynamic stability of the compound is analyzed based on a machine learning model built from an available database of compound formation energies using a DFT simulation database.

5. The system of claim 4, further comprising a new compounds database, a high capacity compounds database and a stable compounds database.

6. The system of claim 4, wherein the molecular descriptors are calculated using one or more of atomic number, an atomic weight, a group number, a period number, an empirical atomic radius, a calculated atomic radius, a covalent radius, Pauling electronegativity, valence, an outer shell s electrons, an outer shell p electrons, an outer shell d electrons, an outer shell electrons, a first ionization energy, a second ionization energy, a third ionization energy, a melting point, a boiling point or density.

7. One or more non-transitory machine readable information storage mediums comprising one or more instructions which when executed by one or more hardware processors cause managing a plurality of events, the instructions cause:
  providing a first set of one or more elements, via an input module;
  providing a second set of one or more elements via the input module;
  generating a plurality of compounds using the first set of one or more elements and the second set of one or more elements based on predefined input conditions, wherein the predefined input conditions comprises: type of compounds, a list of elements in the first set of one or more elements, a list of elements in the second set of one or more elements, and a total number of elements desired in the compound, the type of compounds comprising one of $AB$, $AB_2$, $A_2B$, and $AB_5$, part A being selected from the first set of one or more elements provided and part B being selected from the second set of one or more elements provided that do not constitute A, wherein the plurality of compounds have hydrogen storage capabilities, and wherein generation of the plurality of compounds develops a library of probable compositions using knowledge of existing composition of hydrogen storage materials with high storage capacities;
generating molecular descriptors for the plurality of compounds by extracting compositional information of each of the plurality of compounds, wherein the molecular descriptors effectively describe molecules for the purpose of predicting hydrogen storage capacities of materials, wherein generating the molecular descriptors comprises:
  selecting a subset of elemental descriptors of the molecular descriptors which have an effect on bandgap of materials; and
  generating the molecular descriptors using the subset of elemental descriptors, the molecular descriptors represent each molecule uniquely from the set of elemental descriptors;
generating a machine learning model using the molecular descriptors;
predicting gravimetric hydrogen storage capacity of the generated plurality of compounds using the machine learning model, wherein the machine learning model, is trained based on the molecular descriptors chosen to predict the hydrogen storage capacities of the plurality of compounds, wherein predicting the gravimetric hydrogen storage capacity further comprises providing feedback to improve prediction, and wherein the prediction of the gravimetric hydrogen storage capacity comprises:
  training the machine learning model based on the molecular descriptors for predicting the gravimetric hydrogen storage capacity of the generated plurality of compounds, and
  optimizing the machine learning model by performing a two-stage optimization procedure comprising a three-fold cross validation for estimating a combination of parameters and a grid search on the estimated combination of parameters;
selecting a set of compounds out of the plurality of compounds based on a predefined criteria of gravimetric hydrogen storage capacity, wherein the selecting step reduces total number of probable compounds;
predicting formation energy of each of the set of compounds using a computational database of formation energies;
calculating minimum formation energy of all possible decomposition mixtures of each compound of the set of compounds; and
predicting a compound as thermodynamically stable in response to determining that the formation energy of the compound is less than the minimum of the formation energies of the possible decomposition mixtures of the respective compound, wherein each of the thermodynamically stable compounds is identified as the compound suitable for hydrogen storage, and wherein thermodynamic stability of the compound is analyzed based on a machine learning model built from an available database of compound formation energies using a DFT simulation database.

\* \* \* \* \*